US008469032B2

(12) United States Patent
Farnum

(10) Patent No.: US 8,469,032 B2
(45) Date of Patent: Jun. 25, 2013

(54) AIRWAY POSITIONING DEVICE

(76) Inventor: Timothy J. Farnum, Evergreen, CO (US)

( * ) Notice: Subject to any disclaimer, the term of this patent is extended or adjusted under 35 U.S.C. 154(b) by 683 days.

(21) Appl. No.: 12/704,208

(22) Filed: Feb. 11, 2010

(65) Prior Publication Data

US 2011/0036355 A1 Feb. 17, 2011

Related U.S. Application Data

(63) Continuation-in-part of application No. 12/583,241, filed on Aug. 17, 2009, now Pat. No. 8,347,889.

(51) Int. Cl.

| | |
|---|---|
| ***A61G 17/00*** | (2006.01) |
| ***A61G 15/00*** | (2006.01) |
| ***A61F 5/37*** | (2006.01) |
| ***A61F 11/00*** | (2006.01) |
| ***A61F 5/00*** | (2006.01) |
| ***A47C 1/10*** | (2006.01) |
| ***A47C 20/00*** | (2006.01) |
| ***A61C 5/00*** | (2006.01) |
| ***A63B 23/03*** | (2006.01) |
| ***A01N 1/00*** | (2006.01) |
| ***A47B 7/00*** | (2006.01) |
| ***A61B 1/32*** | (2006.01) |
| ***A61B 1/00*** | (2006.01) |

(52) U.S. Cl.
USPC ........... 128/845; 128/846; 128/857; 128/870; 297/391; 297/392; 297/393; 433/140; 482/11; 27/25.1; 27/13; 5/622; 5/637; 5/638; 600/226; 600/227; 600/228; 600/229; 600/230; 600/231; 600/102; 602/17

(58) Field of Classification Search
USPC .................. 128/845, 848, 857, 866, DIG. 23, 128/DIG. 97, 870, 846; 297/391–393; 433/140; 482/11; 27/25.1, 13; 5/622, 637, 638; 600/238, 600/226–231, 102; 602/17
See application file for complete search history.

(56) References Cited

U.S. PATENT DOCUMENTS

| | | | | |
|---|---|---|---|---|
| 354,976 A | | 12/1886 | Field | |
| 1,131,802 A | * | 3/1915 | Stenshoel | 27/13 |
| 1,441,817 A | | 1/1923 | McCullough | |
| 1,729,525 A | | 9/1929 | Stenshoel | |
| 1,776,167 A | | 9/1930 | Stenshoel | |
| 2,452,816 A | | 11/1948 | Wagner | |
| 3,188,079 A | | 6/1965 | Boetcker et al. | |

(Continued)

OTHER PUBLICATIONS

Select File History from related U.S. Appl. No. 12/583,241, dated Dec. 5, 2011 through Sep. 5, 2012, 48 pages.

(Continued)

*Primary Examiner* — Patricia Bianco
*Assistant Examiner* — Nihir Patel
(74) *Attorney, Agent, or Firm* — Lathrop & Gage LLP

(57) ABSTRACT

An airway positioning device facilitates the maintenance of a patent airway by correctly positioning a patient's head during anesthesia. A flat base supports a supine patient's head. A pair of rails slope downward from a first end of the base to a second end of the base. A track mounts with at least one of the rails. At least one adjustable support arm movably mounts with the track via a locking coupling device at an end of the arm distal to the patient's head. A patient engaging member mounted with an end of the arm proximal to the patient's head supports the patient's head in a desired position during an operation or procedure.

20 Claims, 13 Drawing Sheets

U.S. PATENT DOCUMENTS

| | | | |
|---|---|---|---|
| 4,064,401 | A | 12/1977 | Marden |
| 4,700,691 | A | 10/1987 | Tari et al. |
| 4,867,404 | A | 9/1989 | Harrington et al. |
| 5,524,639 | A | 6/1996 | Lanier et al. |
| 5,865,730 | A | 2/1999 | Fox et al. |
| 5,976,080 | A | 11/1999 | Farascioni |
| 5,984,864 | A | 11/1999 | Fox et al. |
| 6,506,149 | B2 | 1/2003 | Peng et al. |
| 6,581,889 | B2 | 6/2003 | Carpenter et al. |
| 7,182,731 | B2 * | 2/2007 | Nguyen et al. ................ 600/229 |
| 2010/0299835 | A1 * | 12/2010 | Andrews ........................... 5/620 |

OTHER PUBLICATIONS

Medsurplusonline—ACROBAT Mechanical Stabilizer System, retrieved from the Internet Feb. 22, 2010, http://www.medsurplusonline.com/productDetails.php?prodld=4446, 2 pages.

Medtronic Octopus 4 Surgical Solutions, retrieved from the Internet Feb. 22, 2010, http://www.medtronic.com/cardsurgery/products/mics_octopus4.html, 3 pages.

* cited by examiner

AIRWAY POSITIONING DEVICE

RELATED APPLICATIONS

This application is a continuation-in-part of U.S. application Ser. No. 12/583,241, filed Aug. 17, 2009 now U.S. Pat. No. 8,347,889 and incorporated herein by reference.

BACKGROUND OF THE INVENTION

1. Field of the Invention

A positioning device to facilitate the maintenance of a patent airway by correctly positioning the patient's head under anesthesia during an operation or procedure.

2. Description of the Prior Art

Monitored Anesthesia Care (MAC) anesthesia is commonly used as an anesthetic technique. During MAC, sedative, hypnotic and/or anesthetic drugs introduced into the bloodstream are used in combination with a local anesthetic applied to the operative site. MAC anesthesia may be employed in combination with anesthesia such as spinals, epidurals, and peripheral nerve blocks, which also provide temporary loss of feeling and movement at the operative site. An upper airway obstruction may occur when using MAC anesthesia technique because of respiratory depression and/or relaxation of airway musculature caused by the drugs. For example, a fully-relaxed patient's jaw and tongue may slip back and obstruct the airway.

To reduce the risk of an upper airway obstruction, an anesthetist should position the airway to maintain airway patency. In particular, the anesthetist will manually lift the chin upwards and tilt the head. This correctly positions the head with anterior displacement of the mandible with airway structures; this contributes to allowing air to pass from the pharynx into the trachea and allow patient air exchange. Alternatively a jaw-thrust maneuver may be employed by placing hands at both sides of the mandible and thrusting the jaw forward. Either method requires the anesthetist to support the patient's head manually throughout the surgery.

U.S. Pat. No. 1,131,802 shows a device comprising a frame having a pair of angular adjustable side extensions, a vertically adjustable head rest detachably mounted on the frame with freedom for horizontal adjustment longitudinally of the side extensions, and a pair of vertically adjustable jaw rests mounted on the side extensions for movement toward and away from the head rest.

U.S. Pat. No. 1,441,817 relates to an apparatus comprising a base plate and a pair of spaced jaw props adjustable on the base plate at an angle thereto. The jaw props include the sole projections on the base plate, and the base plate being sufficiently narrow so that it may be placed beneath the neck of a corpse and be adjusted longitudinally of the neck of a corpse while the shoulders of the corpse and the head of the corpse rest upon a head board independently of the base plate.

U.S. Pat. No. 1,729,525 teaches a device comprising a vertically adjustable head rest, jaw rests, angularly and lengthwise adjustable supporting means for the jaw rests carried by the head rest, a supporting structure and head rest having a latch to hold the head rest in adjusted position, including a pair of supports hinged to the head rest and a combined coupling and adjusting device for the supports, the jaw rests being vertically and angularly adjustable with respect to supports, the supports further having the forward ends thereof apertured for receiving the jaw rests and carrying at their forward ends clamping devices for maintaining the jaw rests in adjusted position.

U.S. Pat. No. 1,776,167 shows a device comprising an adjustable head rest element including a pair of oppositely disposed downwardly inclined extensions and a vertical post, an adjustable supporting element including an angle shaped pivoted arm arranged below the head rest element, the supporting element including means for latching the arm, an adjustable coupling device between the post and the arm, a pair of angle shaped oppositely extending jaw rest elements, adjustable coupling devices between the jaw rest elements and the extensions and adjustable shoulder drawing down means pivotally and adjustably connected to the extensions.

U.S. Pat. No. 2,452,816 discloses a jaw supporting device comprising a base member, means for securing the base member to and transversely of a table top, abutments upstanding in adjustable spaced opposition from the base member, and means for selectively adjusting the abutments longitudinally of the base member. Also disclosed are a straight cylindrical stem clampably swiveled to extend upwardly from each abutment's upper end, a tubular element telescoped over each stem and slidable axially thereon, means for clamping the tubular element to and in selectively adjusted positions along the stem, a mounting block clampably swiveled to the free end of each tubular element and a jaw engaging cushion removably and replaceable clipped to and in supported relation against each block.

U.S. Pat. No. 4,700,691 relates to a restraining and supporting device for the head of a patient comprising a head immobilizing contraption connected to the operating table, arm and hand supports for the surgeon, wherein the hand supports are fixed to the head immobilizing contraption through flexible arms, also provided with elements releasing or tightening the flexible arms, which elements are fitted to one of the fingers of the surgeon's hand, or interconnected with hand and/or foot switch. The head immobilizing contraption consists of nape support provided with a three-point bearing for the head and can be set at an adjustable height. A front support clamps down the head into the nape support and is connected to the nape support through a hinged mechanism. The flexible arms are attached to the front support of the head immobilizing contraption.

U.S. Pat. No. 5,524,639 discloses an apparatus intended to maintain or improve a supine patient's airway in a hands-free environment. A frame and detachable pillow device are placed under the patient's head. Mechanisms extend laterally from the frame and provide jaw support members that may be brought under the angles of the jaw. The jaw support members may slide towards and away from the frame, but this sliding movement is regulated by a unidirectional clutch, such as a ratchet and pawl system, which restricts the jaw support members to sliding movement away from the frame only. When the jaw support members are slid away from the frame, they engage the angles of the jaw, and then thrust the jaw forward to maintain or improve the patient's airway. Once the desired anteriorly thrust position of the jaw is achieved, the unidirectional clutch holds the jaw in place until the clutch is released. The weight of the jaw then causes the jaw support members to slide back towards the frame, restoring the jaw to its normal position.

SUMMARY

The present invention relates to a positioning device to facilitate the maintenance of a patent airway by correctly positioning a patient's head under anesthesia during an operation or procedure having at least one adjustable support arm including multiple segments or sections configured to be selectively positioned relative to the adjacent segments or sections, a patient engaging member configured to engage the patient coupled to the proximal end portion of the adjustable support arm, a base coupled to the distal end portion of the adjustable support arms, a support arm position retention assembly to selectively secure or lock the adjustable segment arms in a desired position such that the patient engaging member engages and restrains the patient's head from movement during an operation or procedure.

The segments or sections of the adjustable support arms have elements each with a central channel or aperture formed therein to receive a flexible wire or cable therethrough The patient engaging member may be configured to comprise either a chin support or a jaw thrust support.

The support arm position retention assembly includes a flexible wire or cable coupled between the patient engaging member and the base.

As previously described, the adjustable support arms have several segments or sections that can be moved relative to each other to position the adjustable supporting arms to engage the patient's chin or each side of the patient's jaw. The segments or sections of the adjustable support arms include a central channel or aperture to receive a flexible wire or cable therethrough. The length of flexible wire or cable can be loosened or tightened by rotating or turning a positioning or locking knob coupled thereto to adjust the position and secure the position for the adjustable support arms.

To position or manipulate the chin support or jaw thrust supports to engage the head of the patient once the adjustable support arm(s) is/are secured to the base, the positioning or locking knob is rotatable to loosen the flexible wire or cable allowing the entire adjustable support arm(s) to bend, positioning or moving the patient engaging member(s) to engage either the chin or jaw of the patient. Once so positioned, the positioning or locking knob is rotated, tightening the flexible wire or cable drawing the segments or sections together to secure or lock the adjustable support arm(s) in a patient engaging position. To release the patient from the positioning device, the process is reversed.

In one embodiment, an airway positioning device includes a substantially flat base for supporting a supine patient's head. A pair of rails slope downward from a first end of the base to a second end of the base. At least one of the rails supports a track. At least one adjustable support arm movably mounts with the track via a locking coupling device at an end of the arm distal to the patient's head. The arm has a patient engaging member mounted with a proximal end of the arm, for supporting the patient's head in a desired position during an operation or procedure.

In another embodiment, an airway positioning device has a substantially flat base for supporting a supine patient's head, and a pair of rails sloping downward and outward from a first end of the base to a second end of the base. The rails provide shoulder buttresses at the first end, for maintaining position of the supine patient's shoulders. A track mounts with each rail, and an adjustable support arm movably couples with each track. Each support arm has a distal coupling device mounted with an end of the arm distal to the patient's head. The distal coupling device includes a lever for securing the distal coupling device to the track or releasing the distal coupling device from the track. Each support arm further includes a patient engaging member rotatably and pivotally coupled with an end of the arm proximal to the patient's head. The engaging member supports the patient's head in a desired position during an operation or procedure. An internal stiffening wire runs through a channel within each arm. A locking mechanism tightens the wire to secure the arm and patient engaging member in position.

In another embodiment, an airway positioning system includes a pair of rails sloping downward and outward from a first end of a flat base to a second end of the base, and a track configured with at least one of the rails. At least one adjustable support arm movably couples with the rail. Each support arm has a patient engaging member rotatably and pivotally coupled with an end of the arm proximal to the patient's head, for supporting the patient's head in a desired position during an operation or procedure. A sensor senses position of the patient engaging member on a patient. A processor receives signals from the sensor and from external monitoring equipment. From the sensor signal, the processor determines a position of the patient engaging member on the patient. The processor compares the signal from the external monitoring equipment to a threshold value stored in memory. A motor in communication with the processor controls position of the patient engaging member on the patient by controlling movement of the arm. Upon determining that the signal from the monitoring equipment is below the threshold value, the processor activates the motor to move the patient engaging member to a second position, to vary support of the patient's head and improve airway patency.

The invention accordingly comprises the features of construction, combination of elements, and arrangement of parts which will be exemplified in the construction hereinafter set forth, and the scope of the invention is indicated in the claims.

BRIEF DESCRIPTION OF THE DRAWINGS

For a fuller understanding of the nature and object of the invention, reference should be had to the following detailed description taken in connection with the accompanying drawings in which.

DETAILED DESCRIPTION

Figure 1:
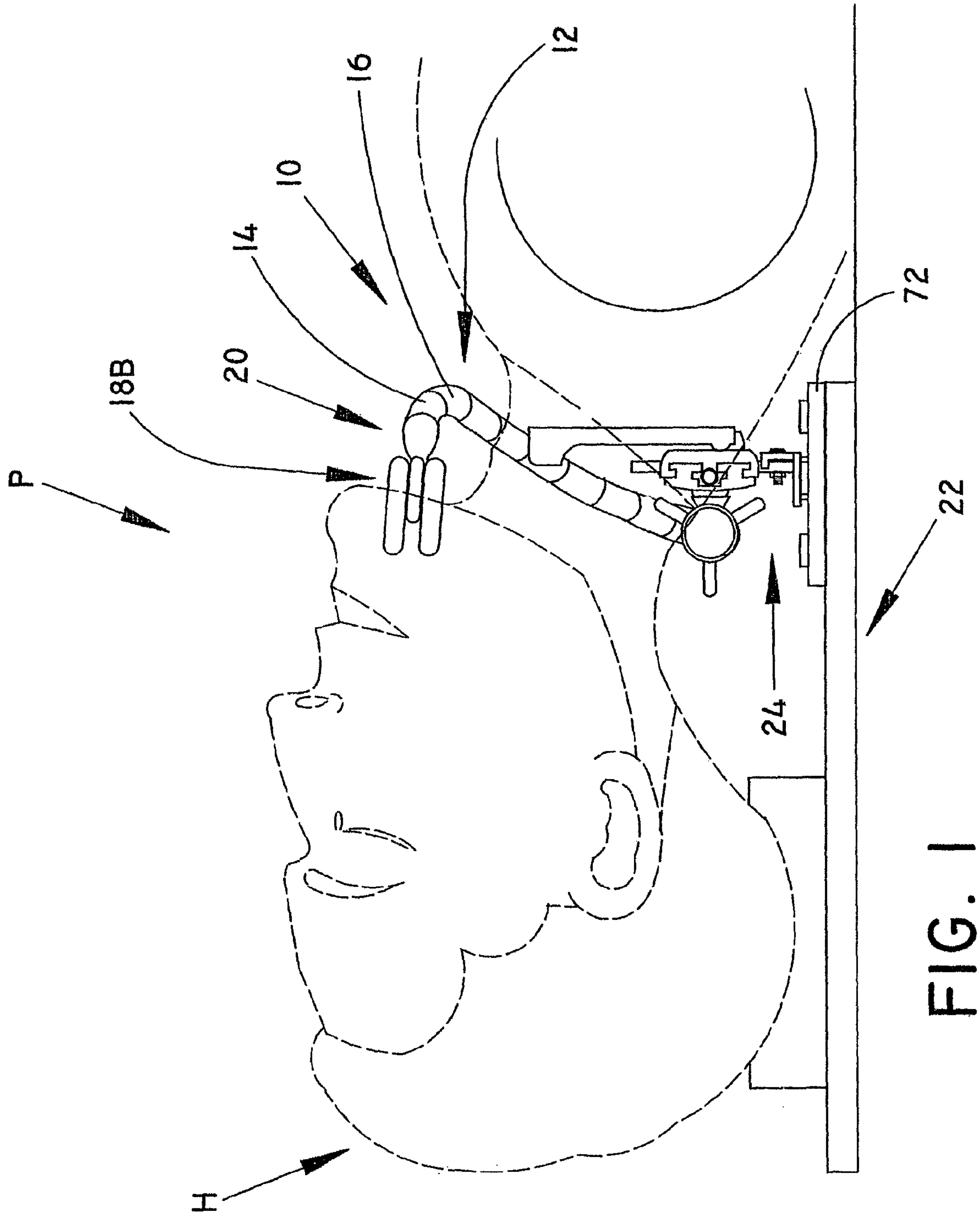
FIG. 1 is a side view of a patient with the positioning device of the present invention positioning the patient's head during an operation or procedure.
Figure 2:
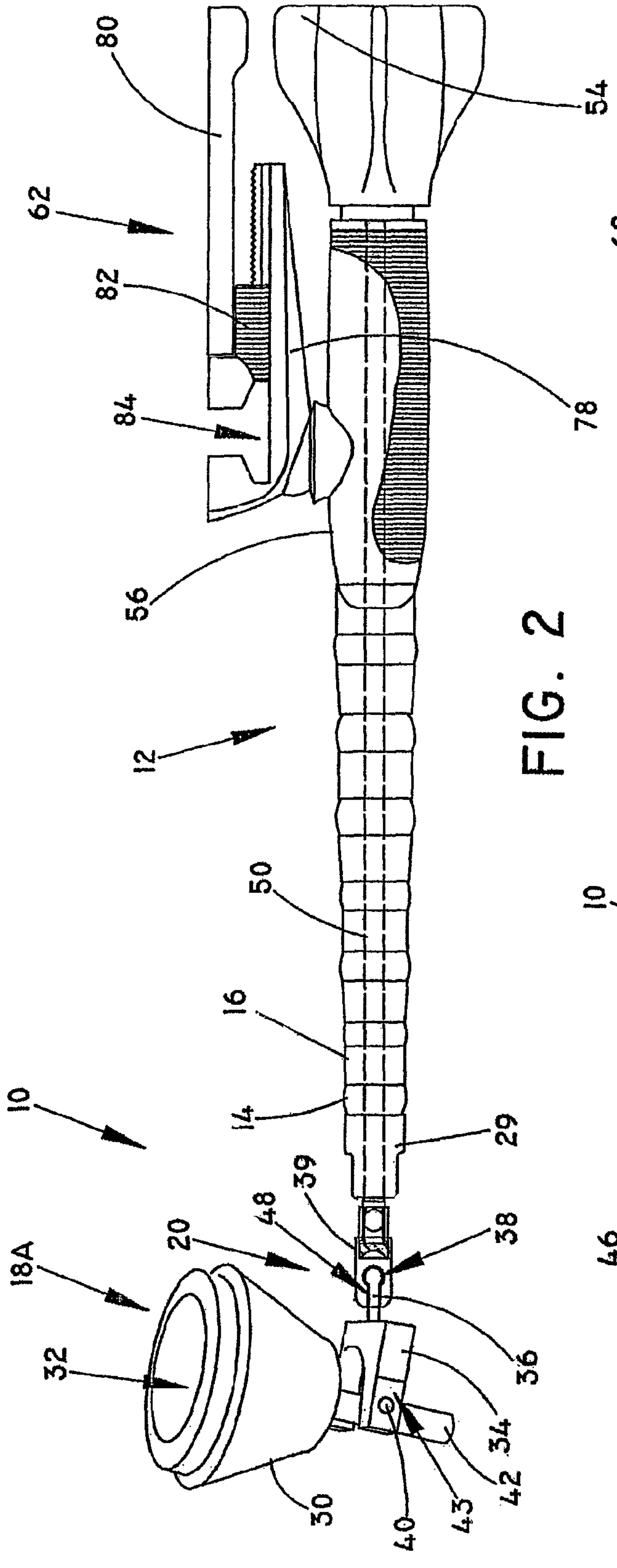
FIG. 2 is a detail view of the adjustable support arm of the present invention with a chin support as the patient engaging member.
Figure 3:
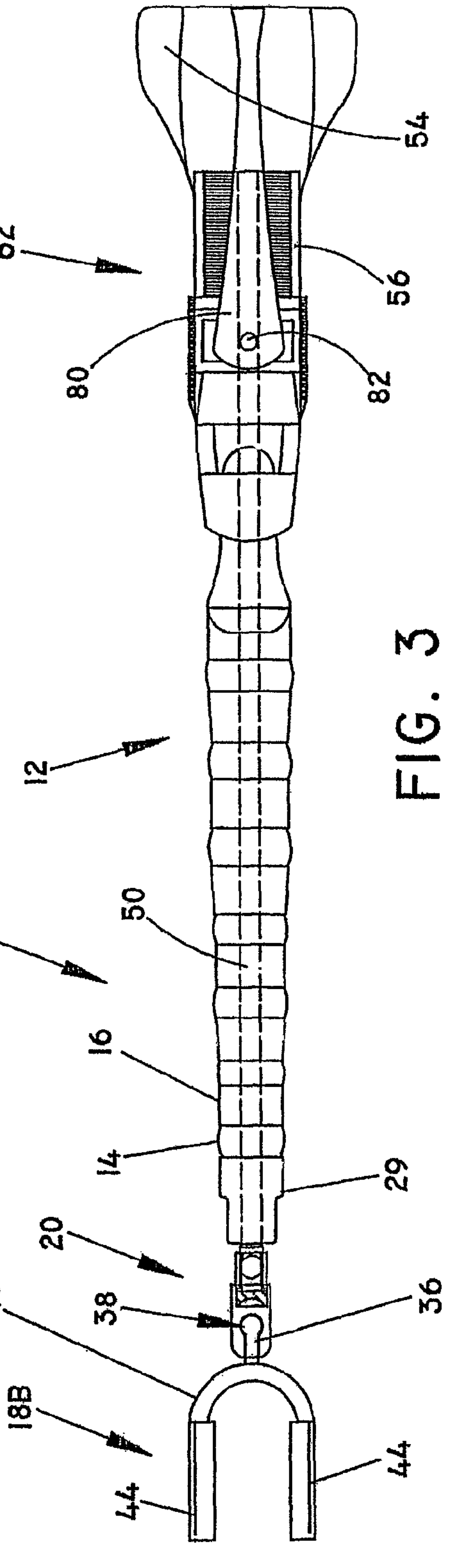
FIG. 3 is a detail view of the adjustable support arm of the present invention with a jaw thrust support as the patient engaging member.

As shown in FIGS. 1 through 3, the present invention relates to a positioning device generally indicated as 10 to maintain a patient's airway by restraining a patient's head H under anesthesia during an operation or procedure comprising at least one adjustable support arm, generally indicated as 12, including a plurality of alternating segments or sections 14 and 16 configured to be selectively positioned relative to the adjacent segments or sections 14 and 16, a patient engaging member generally indicated as 18A or 18B configured to engage the patient P coupled to the proximal end portion of the adjustable support arm 12 by a proximal coupling device generally indicated as 20, a base generally indicated as 22 coupled to the distal end portion of the adjustable support arms 12 by a distal coupling device generally indicated as 24 and a support arm position retention assembly as described hereinafter to selectively secure or lock the adjustable segment arms 12 in a desired position such that the patient engaging member 18 engages and restrains the patient's head H from movement during an operation or procedure. Although the positioning device 10 is described as including the base 22, the distal coupling device 24 can be attached directly to the operating room table or other support (not shown).

Figures 4A, 4B:
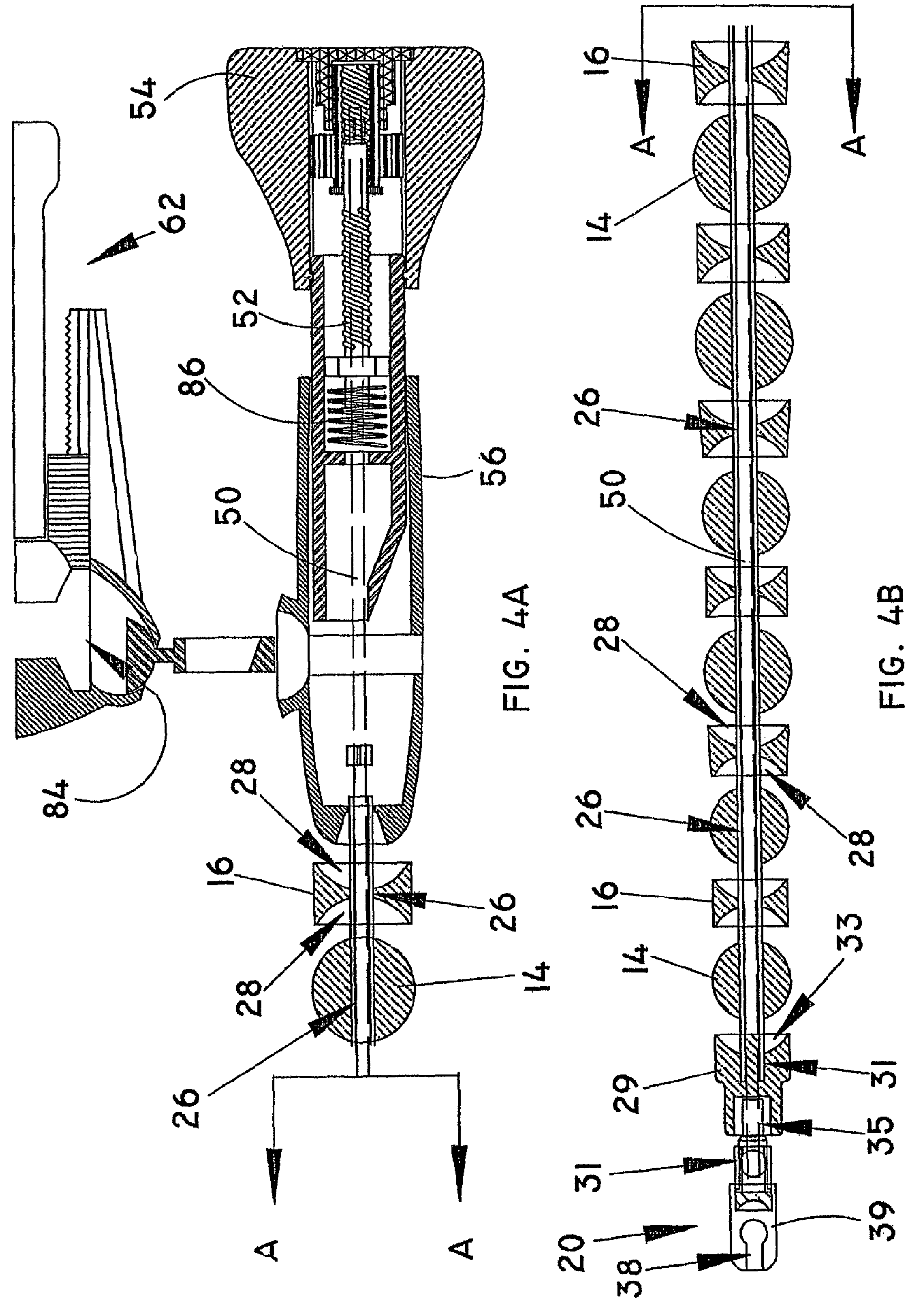
FIGS. 4A and 4B are cross-sectional views of the adjustable support arm of the present invention.

As best shown in FIGS. 4A and 4B, the segments or sections 14 and 16 of the adjustable support arms 12 comprise substantially spherical elements 14 and substantially cylindrical elements 16. A central channel or aperture 26 is formed through each of the substantially spherical elements 14 and each of the substantially cylindrical elements 16 to receive a portion of a flexible wire or cable therethrough described more fully hereinafter. A concave recess 28 is formed on opposite end portions of each substantially cylindrical element 16 to operatively receive a portion of the adjacent substantially spherical elements 14 therein. A proximal intermediate segment or section 29 including a central channel 31 formed through the mid-portion thereof having a concave recess 33 to receive a portion of the outer most substantially spherical element 14 therein with a recess 35 formed on the opposite end portion thereof to receive a portion of the proximal end portion generally indicated as 37 of the adjustable support arm position 12.

The patient engaging member 18 may comprise a chin support 18A as shown in FIG. 2 or a jaw thrust support 18B as shown in FIG. 3.

As shown in FIG. 2 the chin support 18A comprises a chin support body 30 having a concave chin receiving recess 32 formed in the face thereof to receive and support the patient's chin therein to restrain movement of the patient's head H during an operation or procedure. The chin support body 30 is pivotally and rotatably coupled to the proximal end portion of the adjustable support arm 12 by the first coupling member 20. The first coupling member 20 comprises a yoke member 34 rotatably coupled to the proximal intermediate segment or section 29 on the proximal end portion of the adjustable support arm 12 by an interconnecting pin or member 36 partially disposed with a channel and recess 38 formed in a connector element 39 and a mounting pin or member 40 to receive and support a connecting member 42 attached to the rear portion of the chin support body 30 by an aperture 43 to pivotally couple the chin support 18A to the first coupling member 20.

As shown in FIG. 3, the jaw thrust support 18B comprises a jaw engaging member including a pair of substantially parallel spaced apart jaw engaging elements each indicated as 44 extending from a yoke 46 rotatably coupled to the distal end portion of the adjustable support arm 12 by the first coupling member 20 to engage and support one side of a patient's chin to restrain movement of the patient's head H during an operation or procedure. The first coupling member comprises a channel and recess 38 to receive a portion of the interconnecting pin 36. The first coupling member 20 may further include a slot 48 formed in the side thereof to permit the interconnecting pin or member 36 and yoke 46 of the chin support 18A and 18B to pivot.

As shown in FIGS. 2, 3 and 4A, the support arm position retention assembly comprises a flexible wire or cable 50 coupled to the intermediate segment or section 29 at the proximal end portion thereof and to an externally threaded first positioning element 52 extending through the central channel 26 and the concave recesses 28 formed through segments or sections 14 and 16 coupled to the distal end portion thereof disposed to engage an internally threaded positioning or locking knob 54 rotatably mounted on a hollow handle 56 that supports the distal or second coupling member 24 as described hereinafter. Such a support arm position retention assembly is sold under the trade mark Guidant Acrobat™. A similar retention or locking assembly is described in U.S. Pat. No. 4,700,691.

As previously described, the adjustable support arms 12 comprise a plurality of alternating segments or sections 14 or 16 that can be moved relative to each other to position the adjustable supporting arms 12 to engage the patient's chin or each side of the patient's jaw. The segments or sections 14 and the sleeve segments or sections 16 are alternately strung on the flexible wire or cable 50. The length of flexible wire or cable 50 can be loosened or tightened by rotating or turning the internally threaded positioning or locking knob 54, to adjust the position and secure the position for the adjustable support arms 12.

Figure 5:
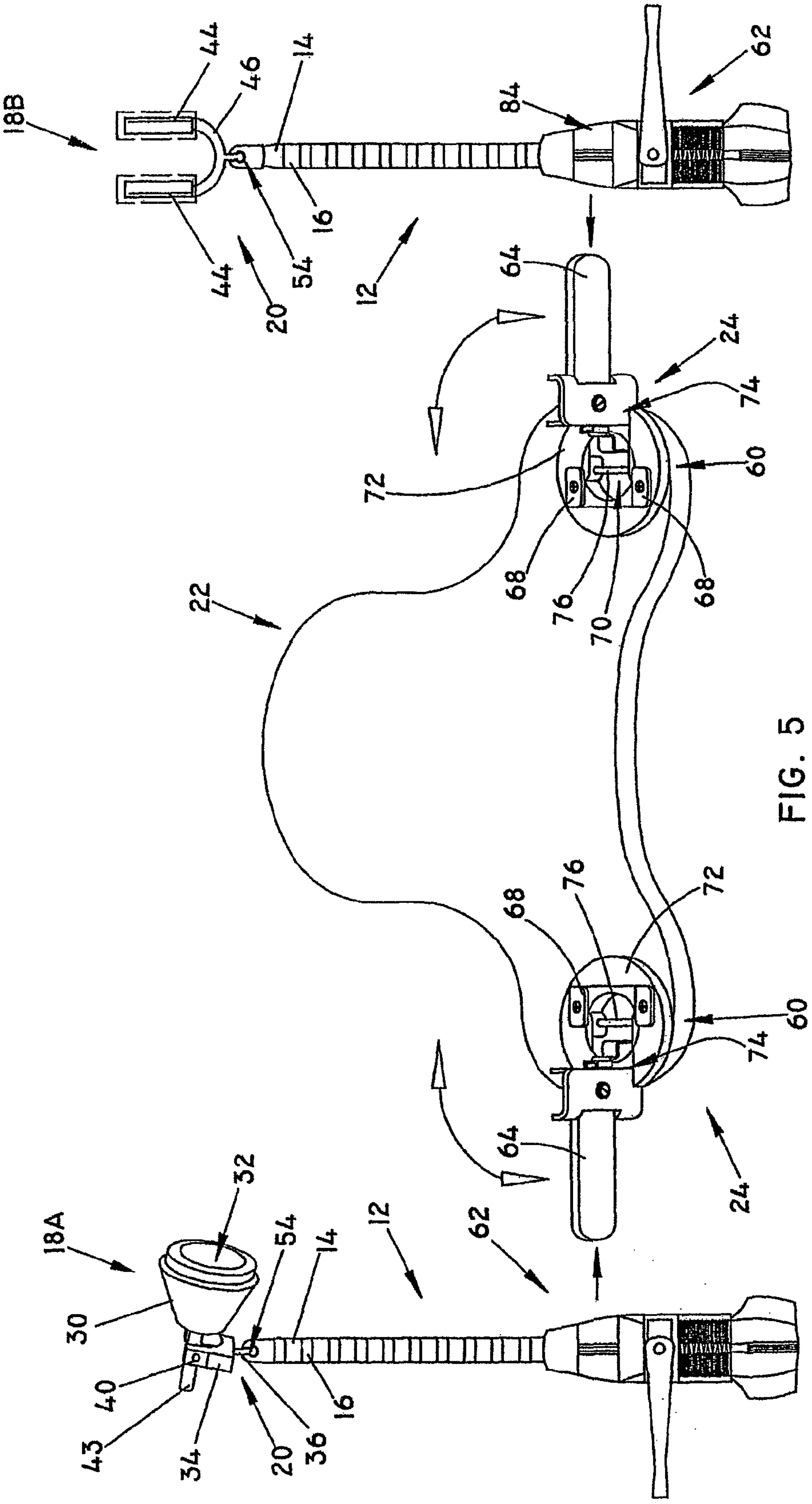
FIG. 5 is a perspective view of the base of the present invention.
Figure 6:
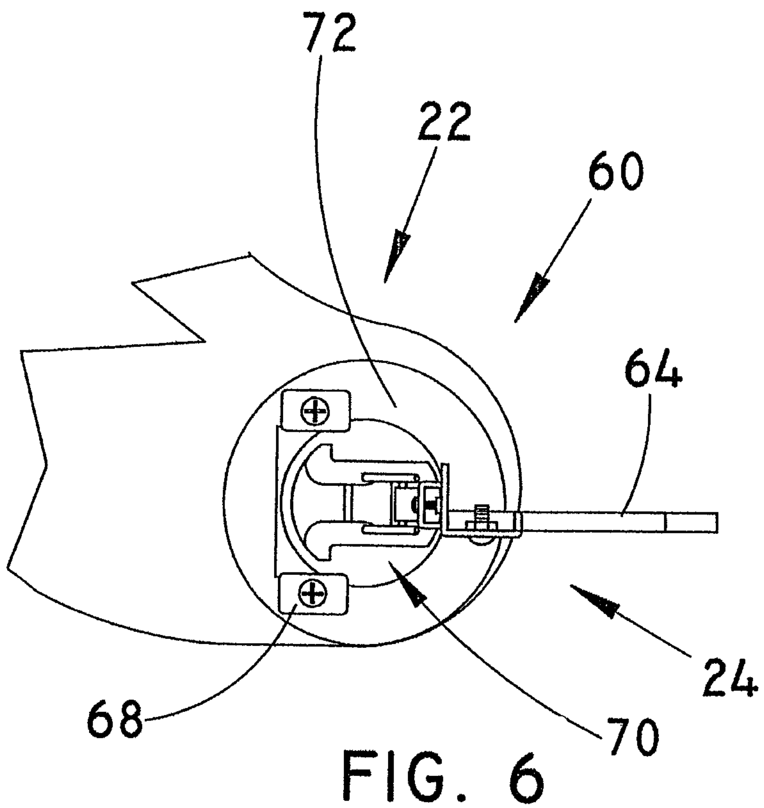
FIG. 6 is a top view of the first distal coupling device of the present invention.
Figure 7:
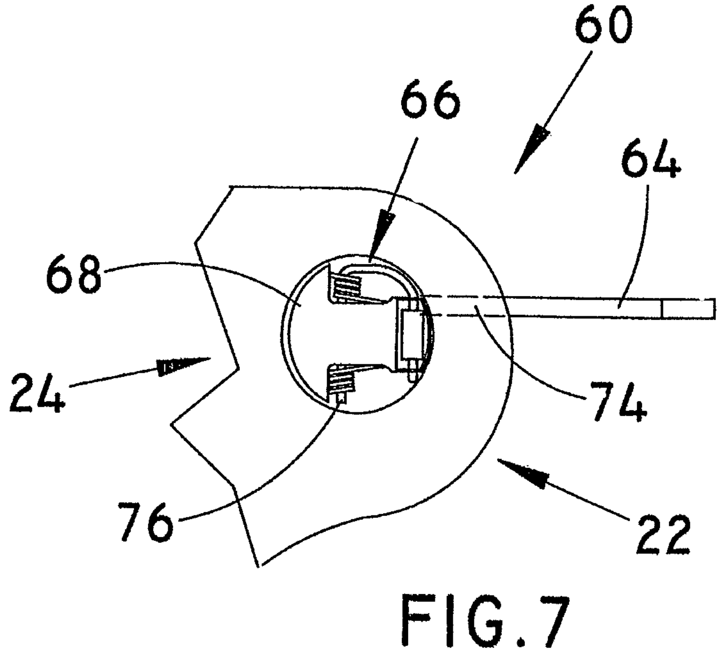
FIG. 7 is a bottom view of the first distal coupling device of the present invention.
Figure 8:
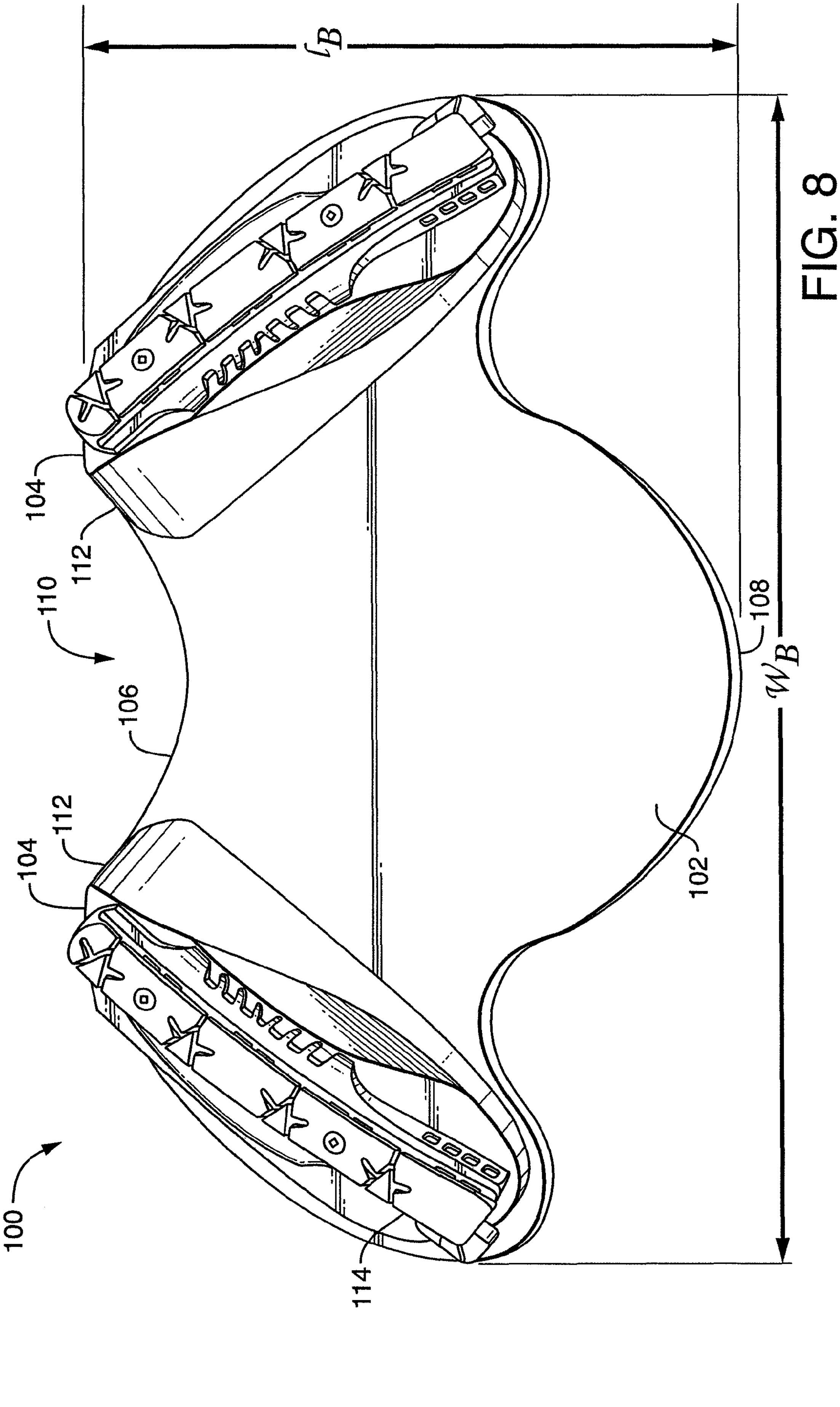
FIG. 8 is a top perspective view of an airway positioning device, according to an embodiment.

The distal coupling device 24 comprises a first distal coupling device and a second distal coupling device generally indicated 60 and 62 respectively. As best shown in FIGS. 5 and 6, the first distal coupling device 60 comprises an attachment member 64 pivotally coupled to the base 22 including a recess or opening 66 by a mounting plate 68 including a recess or opening 70 concentrically aligned with the recess or opening 66 formed with a space 72 including a channel or groove 74 formed on the upper surface thereof. A bias or spring 76 is coupled to the mounting plate 68 by a pin 76 to engage the attachment member 64 to normally retain or maintain the attachment member 64 in a first or operative position. Should the patient awaken and move his/her head laterally the attachment member 64 will be moved to a second or open position, if the lateral force is greater than a predetermined amount or threshold exerted by the patient's head. The second distal coupling device 62 comprises a coupling base 78 mounted to the handle 56 having a handle or lever 80 pivotally coupled thereto between a first or lock position (FIG. 2) and a second or release position (FIG. 3) by a pivot pin 82 to cooperatively form an attachment member slot 84 to receive the attachment member 64 therein to secure the adjustable support arms 12 to the attachment member 64 of the first distal coupling device 60 when in the first or lock position and to release the adjustable support arms 12 from the attachment member 64 of the first distal coupling device 60 when in the second or release position. A bias or spring 86 disposed between a flange 88 and a shoulder 90 formed or mounted to the end portion of the externally threaded first positioning element 52 coupled with the movement of the internally threaded positioning or locking knob 54 to loosen and tighten the flexible wire or cable 50 as described hereinafter.

To position or manipulate the chin support 18A or jaw thrust supports 18B to engage the head H of the patient P once the adjustable support arm(s) 12 is/are secured to the base 22 by the distal coupling device 24 with the first distal coupling device 60 held in the operative position by the bias or spring 76, the internally threaded positioning or locking knob 54 is rotatable to loosen the flexible wire or cable 50 allowing the entire adjustable support arm(s) 12 to bend, positioning or moving the patient engaging member(s) to engage the chin or jaw of the patient P. Once so positioned the internally threaded positioning or locking knob 54 is rotated against the force of the positioning element or bias 86 tightening the flexible wire or cable 50 drawing the segments or sections 14 and 16 together to secure or lock the adjustable support arm(s) 12 in a patient engaging position as shown in FIG. 1. To release the patient from the restraining device 10 the process is reversed.

Since the attachment member 64 is normally retained in the first or operative position by the bias or spring 76 to inhibit lateral movement of the patient's head H unless sufficient lateral force of a threshold or predetermined amount is exerted against the attachment member 64 to overcome the force of the bias or spring 76 moving the attachment member 64 to the second or open position thereby releasing the patient's head H from the constraint of the positioning device 10.

FIGS. 8-11 show an airway positioning device 100 including a base 102 supporting a pair of rails 104 that slope downward and outward from a front, or proximal side 106 of base 102 to a rear or distal side 108 of base 102. Base 102 may be similar to base 22, described above. Base 102 may be manufactured from wood, plastic, hard rubber, closed cell foam, metal or other materials having sufficient rigidity to support rails 104. Base 102 and, optionally, patient contact surfaces of rails 104 (such as shoulder buttresses described herein below) may be padded to enhance patient comfort and/or further facilitate positioning of the patient's head.

In one aspect, base 102 has a width ($w_B$) of about 20-30 inches and a length ($l_B$) of about 10-12 inches. However, one or both of $w_B$ and $l_B$ may vary according to intended use or patient size. For example, both $w_B$ and $l_B$ may be reduced to about 10 inches and about 6 inches, respectively, in a device 100 for use with pediatric patients. Dimensions of rails 104 and tracks, arms and patient support devices used therewith (described below) may be similarly reduced in pediatric models. Optionally, spacing or distance between rails 104 at front side 106 and proximate rear side 108 is customizable. For example, rails 104 are rotatable or otherwise movable with respect to base 102 and lock with base 102 in a variety of positions, for a customized fit with a patient's head, neck and shoulders.

Front side 106 of base 102 is proximal to the shoulders of a supine patient with his head positioned upon base 102, and rear side 108 of base 102 is distal from the patient's shoulders, with respect to front side 106. Front side 106 is shaped with a curve or cutout 110 for accommodating the C7 vertebral prominence in the neck of a supine patient positioned with device 100. Rails 104 are shaped to provide shoulder buttresses 112 at front side 106. Shoulder buttresses 112 aid in maintaining device 100 in position relative to the body of a conscious or unconscious patient while the anesthetist manipulates the head, chin or jaw for optimal airway positioning. For example, shoulder buttresses 112 prevent inferior slippage of device 100 relative to the patient, such as device 100 creeping down beneath the patient's neck and shoulders as tilting, pulling or other positioning force is applied to the head.

Figure 9:
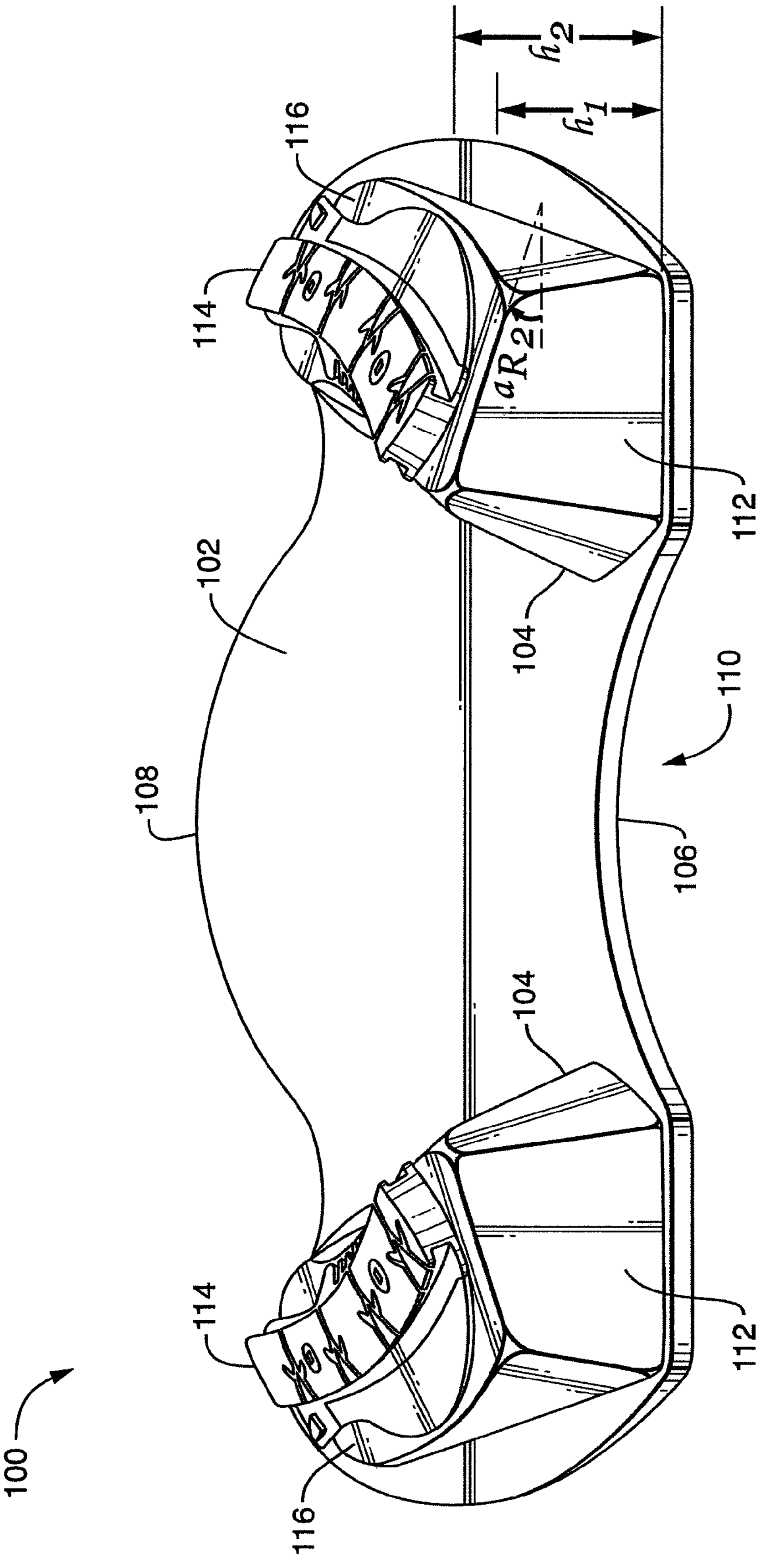
FIG. 9 is a front-top perspective view of the airway positioning device of FIG. 8.
Figure 10:
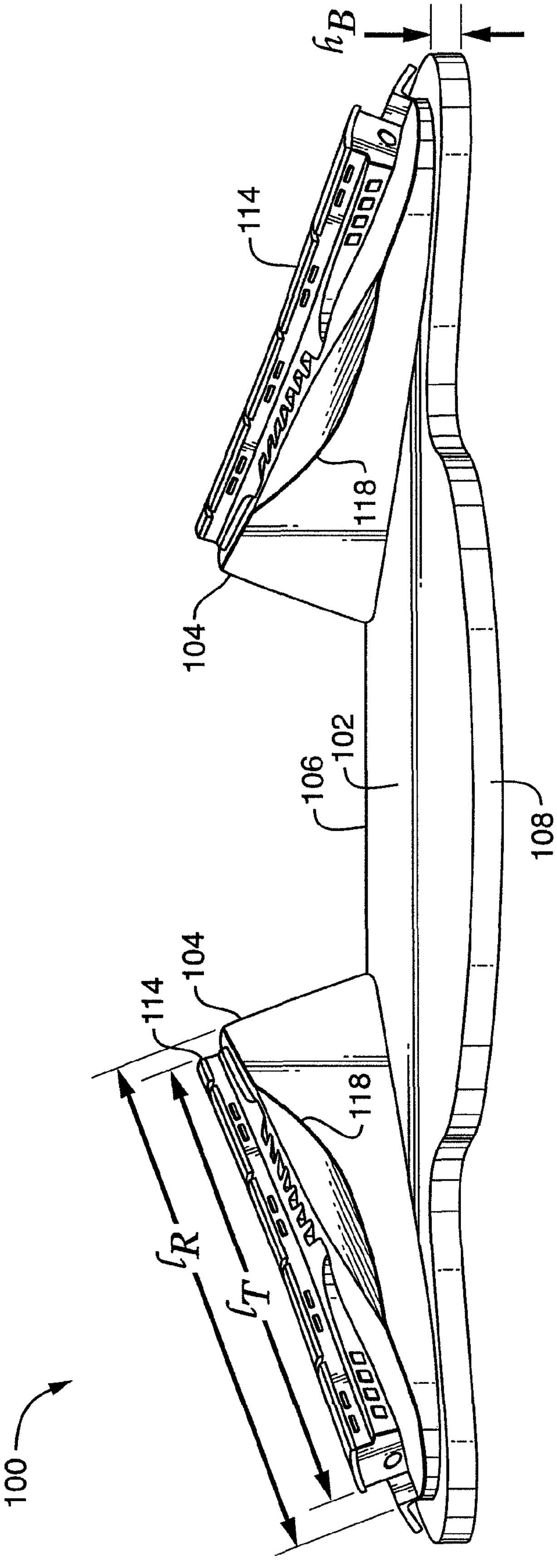
FIG. 10 is a rear perspective view of the airway positioning device of FIGS. 8 and 9.

One or both of rails 104 support a track 114. The front, perspective view of FIG. 9 shows placement of tracks 114 along angled and sloping top surfaces 116 of rails 104. Slope and elevation of rails 104 (and by extension, of tracks 114) may vary; however, in one embodiment, rails form a rail angle ($a_R$) of about 30-45° relative to base 102, from rear side 108 to front side 106 at about 30 (See FIG. 11). Shoulder buttresses 112 and rails 114 have a first height ($h_1$) of about 2.5 inches, tapering center-to-side to a second height ($h_2$) of about 1.5 inches. The taper from $h_1$ to $h_2$ provides an angled top rail surface 116, set at an acute angle ($a_{R2}$) of about 30-50° with respect to a plane parallel to base 102. The slope of top surface 116, provided by angle $a_{R2}$, increases working space between a patient's head and tracks 114, to better accommodate an anesthetist's hands and to facilitate access to the patient's head and/or to tracks 114. An inner cutaway or slope 118, shown in FIG. 10, provides additional access space between the patient's head and tracks 114/rails 104. As also shown in FIG. 10, base 102 has a height ($h_B$) of about ¼-½ inch. Rails 104 have a first, outer length ($l_{R1}$) of about 7.5 inches. Rails 104 curve or taper to a second, inner length ($l_{R2}$) of about 6.5 inches. Rails 104 measure about 3 inches across at shoulder buttresses 112 and proximate base 102. Track 114 has a length ($l_T$) of about 7.5 inches. It will be appreciated that heights $h_B$ and $h_3$ and lengths $l_{R1}$, $l_{R2}$ and $l_T$ may vary according to design preference or intended use. For example, an extra large model of device 100 may include elevated rails with rail height $h_1$ of about 6 inches, to compensate for height provided by fat pads at the base of the neck and shoulders in an obese individual.

Figure 11:
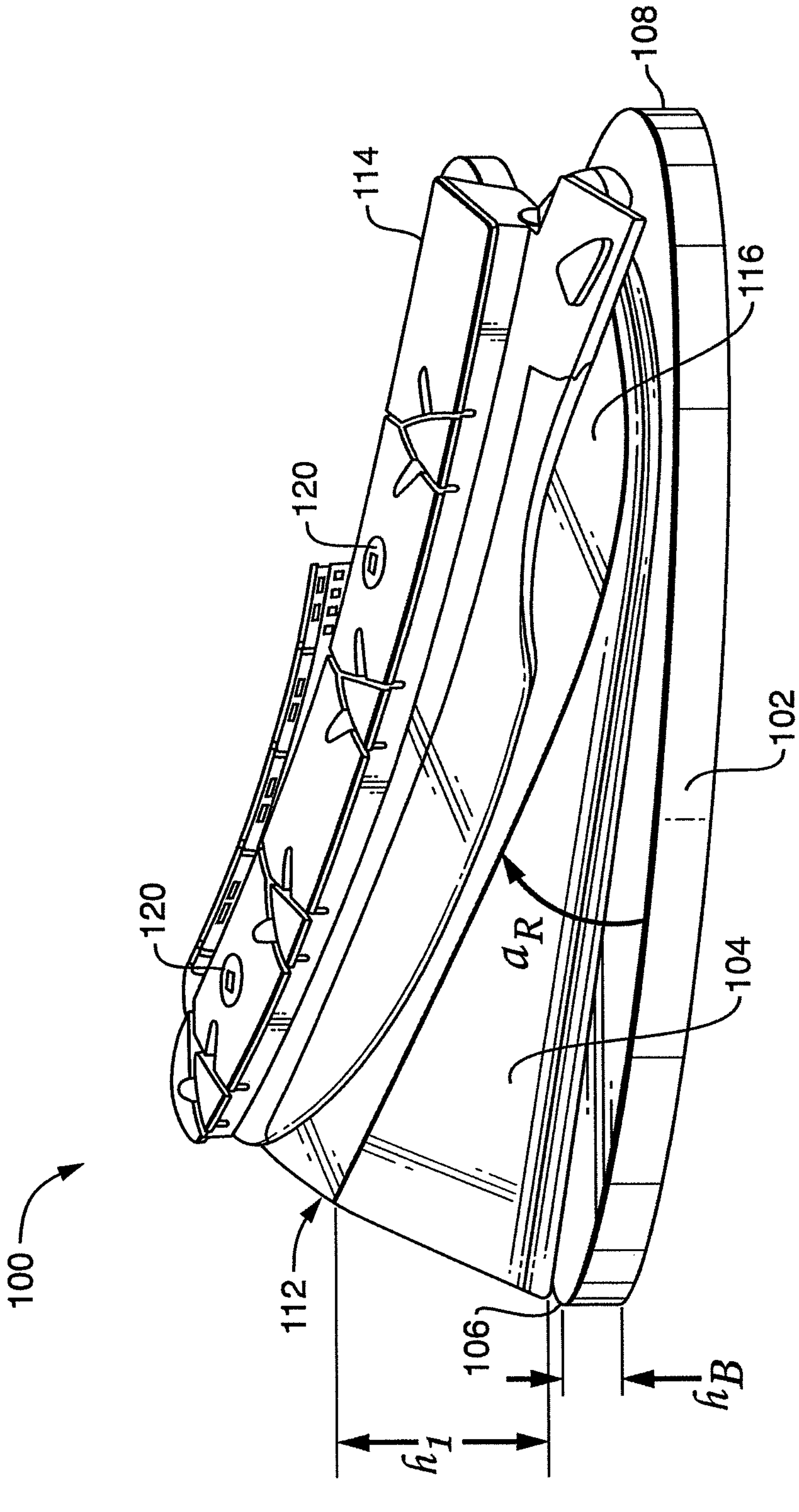
FIG. 11 is a side view of the airway positioning device of FIG. 8.

Track 114 is secured with rail 104 via one or more fasteners 120, shown in side view FIG. 11.

Figure 12:
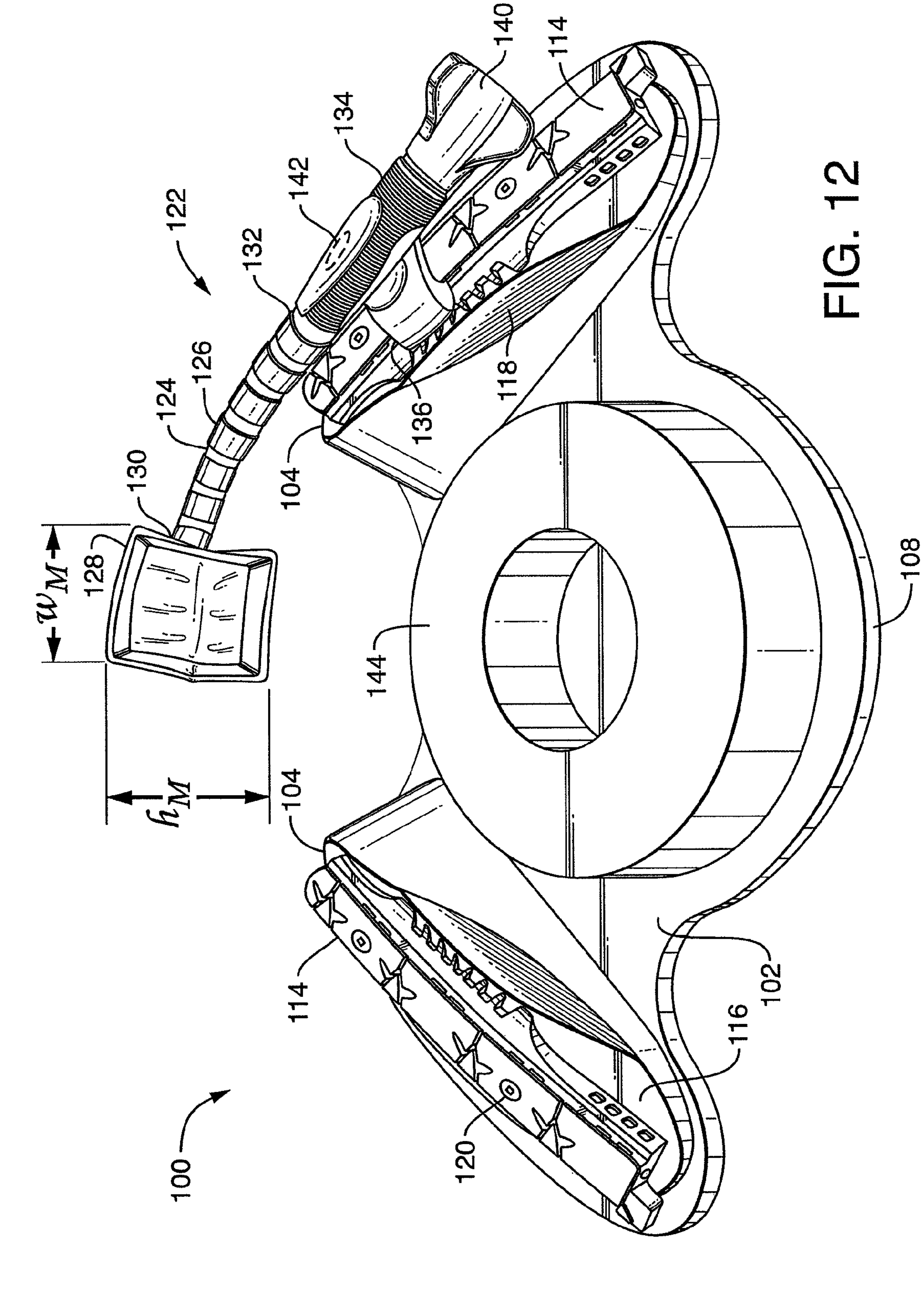
FIG. 12 is a top perspective view of the airway positioning device of FIGS. 8-11, including an adjustable support arm and head support, according to an embodiment.
Figure 13:
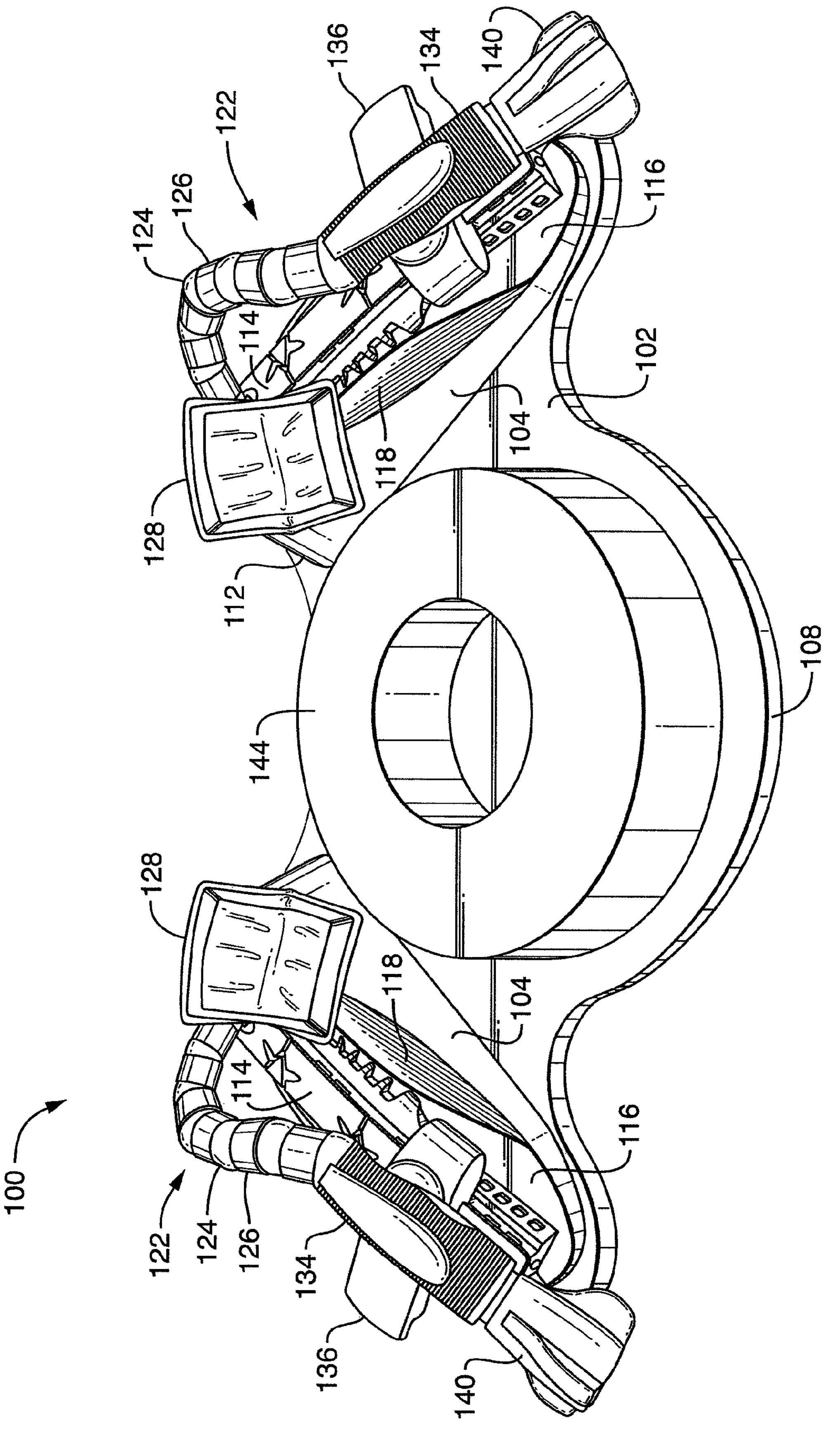
FIG. 13 is a second top perspective view of the airway positioning device of FIG. 11, with a second additional adjustable support arm.
Figure 14:
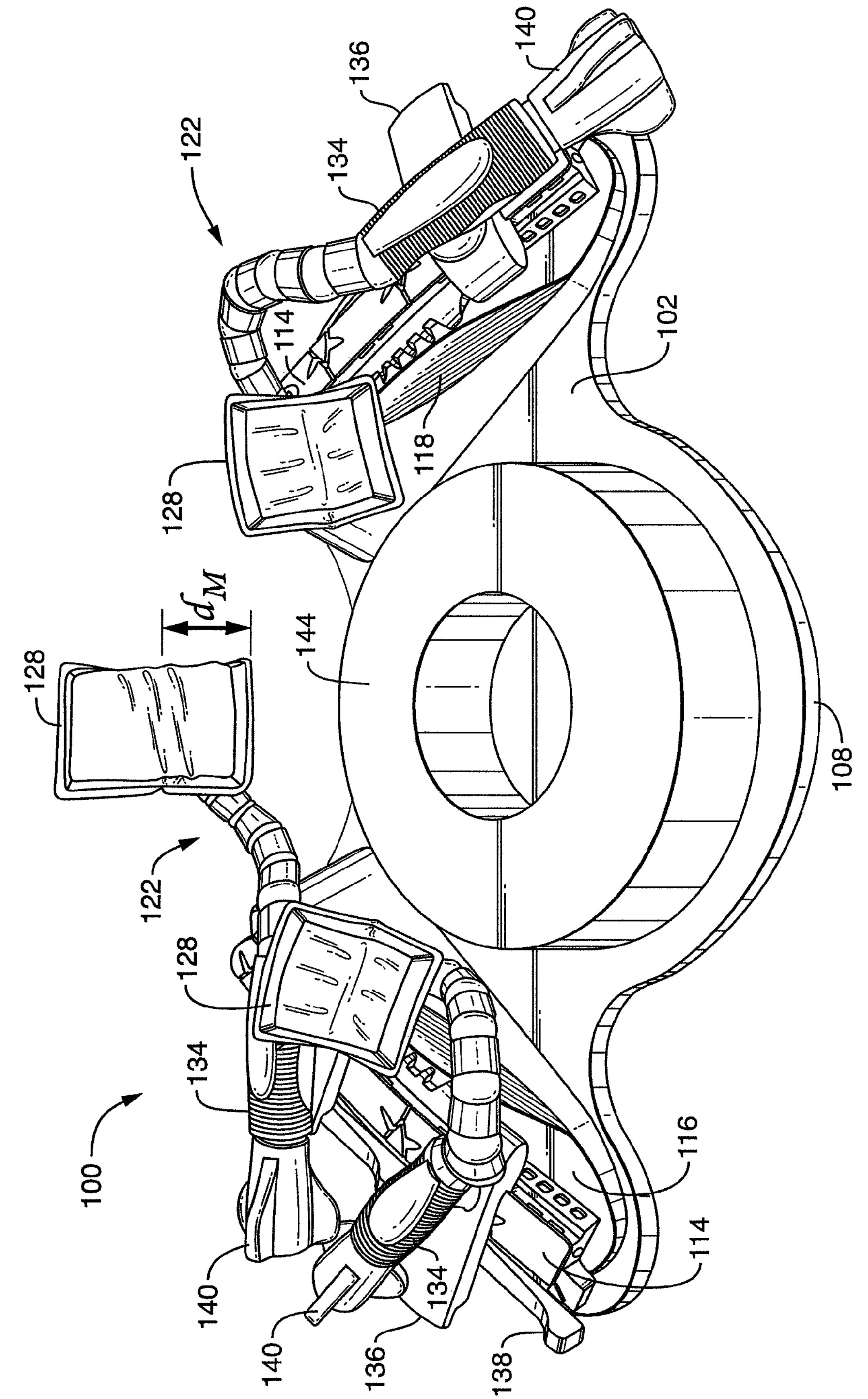
FIG. 14 is a further top perspective view of the airway positioning device of FIG. 11, with a third adjustable support arm.

As shown in FIGS. 12-14, device 100 includes one or more adjustable arms 122 having alternating flexible, linking segments 124 and 126. A patient engaging member 128 rotatably couples with a proximal end 130 of arm 122 (end 130 is proximal to the patient, with respect to a distal arm end 132). In one aspect, patient engaging member 128 is a padded, "chair" shaped member having an angle of about 90° to about 120°, allowing support and maintenance of patient head position at the chin, jaw or elsewhere. Rotation and pivoting action of patient engaging member 128 on arm 122 allows a practitioner to optimally place member 128 to effect a chin lift, jaw thrust or other desired position for maintaining airway patency. Patient engaging member 128 has a width ($w_M$), a height ($h_M$) and a depth ($d_M$, see FIG. 13) each of about 1.5". Internal patient-contact surfaces of patient engaging member 128 are coated with about a ½ inch thick gel pad, foam or other type of padding for patient comfort.

A handle 134 coupled with arm 122 at distal end 132 mounts with a distal coupling device 136 for adjustably coupling arm 122 with track 114. Distal coupling device 136 loosens slightly from and may be moved along track 114 when a lever 138 (see FIG. 13) is in a first position, and is tightened upon and secured in place along track 114 when lever 138 is switched to a second position.

An internal stiffening wire or cable (not shown) runs through a central channel in arm 122. A locking shuttle or knob 140 is rotated to tighten the internal wire and secure arm 122 and patient engaging member 128 in a desired position. When knob 140 is turned to the left, the internal wire loosens, arm 122 slackens and droops, and patient engaging member 128 is both rotatable and pivotable upon arm 122. When arm 122 is slack, segments 124 and 126 may each pivot and/or rotate with respect to one another. Arm 116 is for example a flexible ball-and-collar line with segments 124 and 126 similar to spherical and cylindrical elements 14 and 16 of arm 12, described above.

When knob 140 is turned to the right, the internal stiffening wire tightens and arm 122 and patient engaging member 128 lock into a position into which they have been placed. Arm 122 and its component parts (e.g., internal wire, internal wire interface features, segments 124 and 126, handle 134 and knob 140) may be better understood by reviewing arm 12 in FIGS. 2-4B and the above description thereof. Arm 12 may be substituted for arm 122, and vice versa. For example, the Guidant Acrobat™ Mechanical Stabilizer System may provide track 114, arm 122 and its component parts and distal coupling device 136. Alternately, arm 122 and associated features may be similar to the flexible, u-link arm of the Medtronic Octopus®.

Optionally, knob 140 is done away with and its functionality replaced by an alternate locking mechanism such as a button, a sliding or flip switch or a lever which may be placed on handle 134, for example at position 142. The alternate locking mechanism (hereafter, locking mechanism 142) activates a motor that rotates an internally threaded member, such as externally threaded element 52 of arm 12 (see FIG. 4A), to wind the internal wire about the threaded member, or to unwind the wire from the member, to tighten or loosen the wire and to respectively lock or release arm 122 position. Alternate locking mechanism 142 is activated with a thumb or finger, allowing an anesthetist for example to adjust and hold a patient's chin or jaw position with the left hand and with the right hand to position patient engaging member 128 and (optionally) arm 122, and to activate alternate locking mechanism 142 with a free finger or the thumb of the right hand, without releasing patient engaging member 128 and arm 122 from the desired position. Optionally, alternate locking mechanism 142 may be located on base 102, and in communication with the motor (for rotating the internally threaded member) via a wire.

An additional head support 144 enhances the maintenance of the patient's head position. Support 144, as shown, is doughnut shaped with a central aperture for accommodating the back of a patient's head. However, support 144 may alternately be formed as a continuous cushion or a roll-type pillow for supporting the upper neck or base of the skull. Support 144 may be permanently mounted with base 102, or removably mounted with base 102 via Velcro, reusable adhesive, snaps or other fasteners, or no fasteners at all, to allow for easy removal and cleaning between patients. Support 144 may be made of foam, cloth, rubber or soft plastic, and may optionally be gel filled to provide a custom fit to the patient's head.

As shown in FIG. 13, each rail 114 supports an arm 122 with patient engaging member 128, mounted with a distal coupling device 136. One or more adjustable arms 122 on either side of the patient's head allows for various combinations of support positions. For example, patient engaging members 128 may be placed on either side of the patient's jaw to support a jaw thrust position. Optionally, one member 128 maintains a chin lift while the second member 128 exerts downward force on the patient's forehead, to further support the chin lift position. In another example, opposing support arms 122 and patient engaging members 128 are placed to maintain a jaw thrust position while a third arm and member 122, 128 supports a chin lift position. See, e.g., FIG. 14 showing an embodiment of device 100 with three arms 122.

Figure 15:
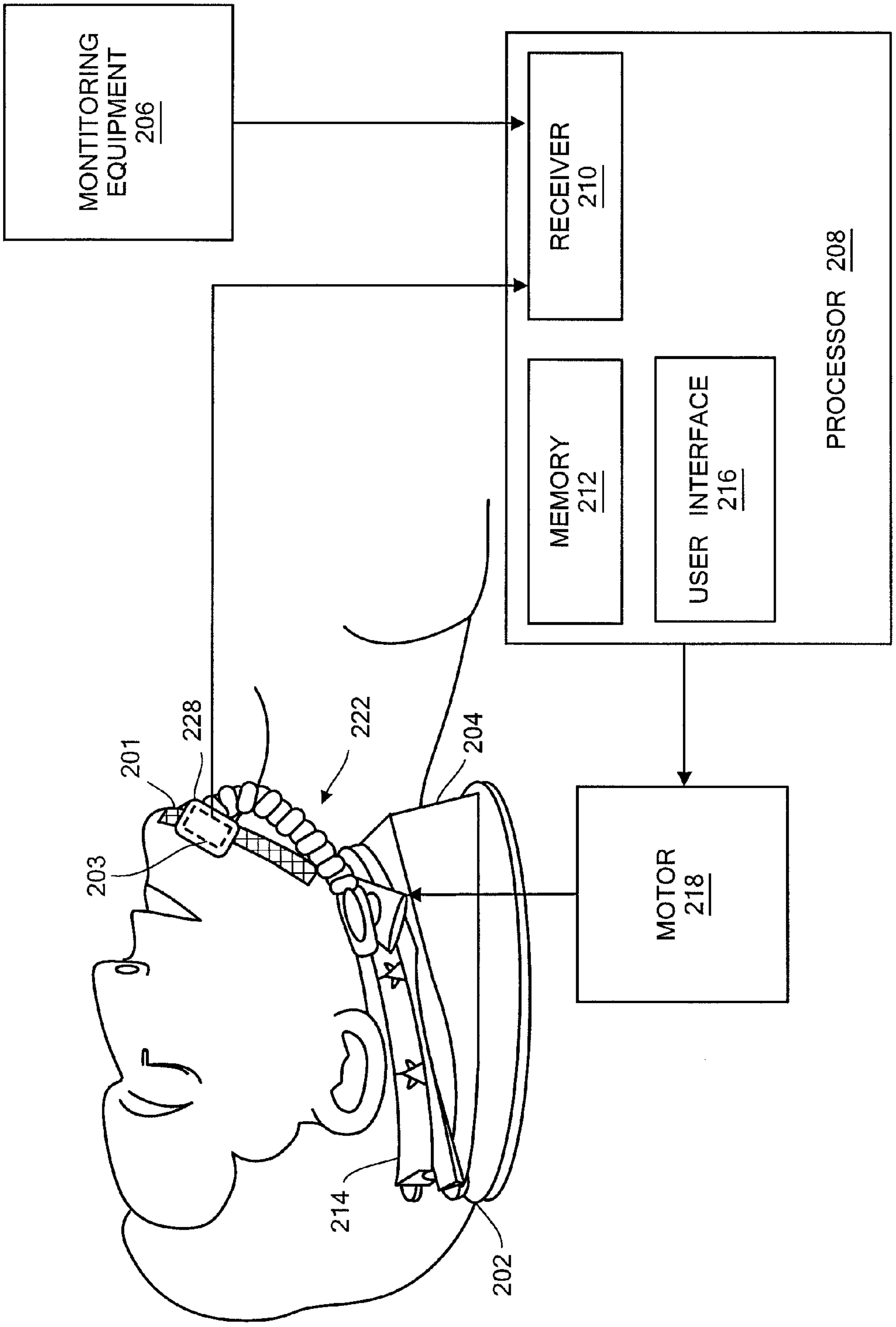
FIG. 15 is a schematic illustration of an airway positioning system including a processor and motor for automatic control of airway positioning.

In one embodiment, schematically shown in FIG. 15, an airway positioning system 200 detects position of patient engaging member or members 228 on a patient via a strip 201 having markers or a grid placed along the patient's jaw line. One or more sensors 203 for detecting the markers or grid positions of strip 201 are mounted with one or more inner, patient-contacting surfaces of patient engaging member 228. External patient monitoring equipment 206, such as a $CO_2$ sensor, heart rate sensor or pulse oximeter communicates with a processor 208, which in turn communicates with one or more robotic adjustable arms 222 coupled with patient engaging members 228. Robotic arm 222 is controlled via a processor 208, which includes a receiver 210 for receiving a signal (e.g., the output) from external monitoring equipment 206. Processor 208 compares the signal from monitoring equipment 206 with a threshold value, which may be preprogrammed into a memory 212 of processor 208 or entered by an anesthetist via an external keypad, touch pad or other user interface 216, and stored in memory 212. If the signal from external monitoring equipment 206 (e.g., a pulse oximeter) falls outside of a desired range, processor 208 reviews signals from marker-detecting sensor 204 to determine (a) placement of patient engaging member 228 on the patient's head, as indicated by the markers contacting or proximate sensor 204, and (b) how patient engaging member 228 and robotic arm 222 may be adjusted to open the airway. Alternately, processor 208 "knows" position of patient engaging member 228 relative to the patient's head upon placement of patient engaging member 228 on strip 201 and, in the event of a sub-threshold value, determines if adjustments can be made.

If, for example, two robotic arms 222 with patient engaging members 228 are supporting the patient's head at a first position proximate the chin and the patient's oxygen saturation falls below a threshold level, processor 208 determines that a second support position (e.g., at the posterior jaw), indicated by markers on strip 201 could be attempted. If a second support position is available, the anesthetist may be notified of the second position via user interface 216. For example, a visual or auditory alarm at user interface 216 attracts the anesthetist's attention and the second position is displayed on a display of user interface 216. The anesthetist may press a button, touch the display or otherwise confirm that the second position should be tried. Upon receipt of a command from the anesthetist, or optionally, automatically, processor 208 controls a motor 218 in communication with arm(s) 222 and patient engaging members 228 to move arms 222 and members 228 from the first position, along strip 201, worn along the patient's jaw, to a marker on strip 201 at the second position. For example, each arm 222 mounts with a distal coupling device 236 on a track 214, mounted on a sloping rail 204, and motor 218 moves distal coupling device 236 along track 214 to reposition arms 222 and patient engaging members 228 and adjust the patient's head position. In this manner, device 200 facilitates automatic transitioning from a first support position to a second support position (i.e., from a chin lift to a jaw thrust) if airway patency becomes compromised or could be improved.

In one aspect, processor 208 receives input from a pulse oximeter. If signals from the pulse oximeter fall below a threshold value or range, processor 208 activates motor 218 (automatically or following confirmation by the anesthetist) to reposition arms 222 and patient engaging members 228 to adjust the patient's airway position. In another aspect, processor 208 receives signals from a heart rate monitor or a $CO_2$ monitor, and initiates repositioning if the received signals exceed a threshold value or range. System 200 optionally generates an alarm upon receipt of any sub- or supra-threshold signals.

Rails 204 with tracks 214, distal coupling devices 236 and arms 222 may mount with a base 202. Components 202, 204, 214, 222 and 236 are for example similar to components 102, 104, 114, 122 and 136 of device 100 and may be further understood by reviewing the above description of device 100. Processor 208 may be a microprocessor, and processor 208 and/or motor 218 need not be separate from the assembly of base 202, rails 204, tracks 214, arms 222 and associated mounting and patient support components, as is shown in FIG. 15 for clarity of illustration. Rather, processor 208 and/or motor 218 may be mounted with base 202, housed within, beside or upon a rail 204 or otherwise configured proximate arms 222.

Certain changes may be made in the above described devices and systems without departing from the scope of the invention. For example, commercially available arms such as models AL5A, AL5B, AL5C or AL5D by Lynxmotion, Inc. may be used in device 100. It is intended that all matter contained in the above description or shown in the accompanying drawings shall be interpreted as illustrative, and not in a limiting sense. It is also to be understood that the following claims are intended to cover all of the generic and specific features of the invention herein described, and all statements of the scope of the invention which, as a matter of language, might be said to fall therebetween.

What is claimed is:

1. An airway positioning device, comprising:
- a substantially flat base for supporting a supine patient's head;
- a pair of rails sloping downward from a first end of the base to a second end of the base;
- a track configured with at least one of the rails; and
- at least one adjustable support arm movably coupled with the track via a locking coupling device at an end of the arm distal to the patient's head, the arm comprising:
  - a patient engaging member mounted with an end of the arm proximal to the patient's head, for supporting the patient's head in a desired position during an operation or procedure;
  - an internal stiffening wire running through a channel within the arm, and
  - a locking mechanism for tightening the wire to secure the arm and patient engaging member in position, the locking mechanism selected from the group consisting of a lever, a switch and a button, the lever, switch or button activating a motor to tighten or loosen the wire.

2. The device of claim 1, the rails sloping outward from the first base end to the second base end, to accommodate the patient's head; an end of each rail providing a shoulder buttress at the first base end, for maintaining position of the patient's shoulders relative to the device.

3. The device of claim 1, the patient engaging member being rotatably and/or pivotally mounted with the proximal end of the arm.

4. The device of claim 2, the patient engaging member comprising a padded support having an obtuse internal angle, for receiving and supporting the patient's jaw or chin to maintain the patient's head in the desired position.

5. The device of claim 1, the base including a cutout at the first end, for accommodating the patient's C7 prominence.

6. The device of claim 1, the arm comprising a plurality of segments, each segment selectively positionable relative to adjacent segments.

7. The device of claim 1, including a track configured with each rail and at least one of the adjustable support arms movably mounted with each track; the patient engaging members of each akin configured for engaging opposite sides of the patient's jaw, to effect a jaw thrust maneuver.

8. The device of claim 1, the base and rails comprising a material selected from the group of wood, plastic, hard rubber and metal.

9. The device of claim 8, wherein at least the base includes a padded patient contact surface.

10. The device of claim 1, further comprising a head support configured with or removably coupled with the base.

11. An airway positioning device, comprising:
- a substantially flat base for supporting a supine patient's head;
- a pair of rails sloping downward and outward from a first end of the base to a second end of the base, the rails providing shoulder buttresses at the first end, for maintaining position of the supine patient's shoulders;
- a track configured with each rail; and
- an adjustable support arm movably coupled with each rail, each support arm having:
  - a distal coupling device mounted with an end of the arm distal to the patient's head and including a lever for securing the distal coupling device to, or releasing the distal coupling device from, the track;
  - a patient engaging member rotatably and pivotally coupled with an end of the arm proximal to the patient's head, for supporting the patient's head in a desired position during an operation or procedure;
  - an internal stiffening wire running through a channel within the arm, and
- a locking mechanism for tightening the wire to secure the arm and patient engaging member in position, the locking mechanism selected from a lever, a switch or a button, the lever, switch or button activating a motor to tighten or loosen the wire.

12. The device of claim 11, the patient engaging member comprising a padded support having an obtuse internal angle, for receiving and supporting the patient's jaw or chin to maintain the patient's head in the desired position.

13. The device of claim 11, the base including one or both of (a) a cutout at the first end, for accommodating the patient's C7 prominence, and (b) a padded patient contact surface.

14. The device of claim 11, the arm comprising a plurality of segments, each segment selectively positionable relative to adjacent segments.

15. The device of claim 11, the patient engaging member of each aim configured for engaging opposite sides of the patient's jaw, to effect a jaw thrust maneuver.

16. The device of claim 11, the base and rails comprising a material selected from the group of wood, plastic, hard rubber and metal.

17. The device of claim 11, further comprising a head support configured with or removably coupled with the base.

18. An airway positioning system, comprising:
- a pair of rails sloping downward and outward from a first end of a flat base to a second end of the base;
- a track configured with at least one of the rails;
- at least one adjustable support arm movably coupled with the rail, each support arm having a patient engaging member rotatably and pivotally coupled with an end of the arm proximal to the patient's head, for supporting the patient's head in a desired position during an operation or procedure;
- a sensor configured with the patient engaging member for sensing position of the patient engaging member on a patient;
- a processor for receiving a signal from the sensor and from external monitoring equipment, the processor determining from the sensor signal a position of the patient engaging member on the patient, and comparing the signal from the external monitoring equipment to a threshold value stored in memory; and a motor in communication with the processor and controlling position of the patient engaging member on the patient by controlling movement of the aim;

wherein upon determining that the signal from the monitoring equipment is below the threshold value, the processor activates the motor to move the patient engaging member to a second position, to vary support of the patient's head and improve airway patency.

19. System of claim 18, the sensors of the patient engaging members configured for detecting markers on a strip applied to the patient's jaw line and transmitting signals identifying the markers; the processor determining position of the patient engaging members on the patient's jaw from the signals.

20. System of claim 18, each arm mounted with a distal coupling device for securing to the track at a plurality of track positions, the motor controlling movement of the arm by controlling movement of the distal coupling device between the track positions.

* * * * *